United States Patent [19]
Winkler

[11] 3,938,391
[45] Feb. 17, 1976

[54] SAMPLING DEVICE FOR LIQUEFIED GASES

[75] Inventor: Dietmar Winkler, Munich, Germany

[73] Assignee: Linde Aktiengesellschaft, Wiesbaden, Germany

[22] Filed: Feb. 19, 1975

[21] Appl. No.: 551,139

[30] Foreign Application Priority Data
Feb. 23, 1974 Germany............................ 2408845

[52] U.S. Cl................................. 73/421.5 R; 62/55
[51] Int. Cl.²............................................ G01N 1/22
[58] Field of Search..................... 73/421.5 R; 62/55

[56] References Cited
UNITED STATES PATENTS
3,123,982  3/1964  Brown et al..................... 73/421.5 R Primary Examiner—S. Clement Swisher
Attorney, Agent, or Firm—Millen, Raptes & White

[57] ABSTRACT

A device for sampling liquefied gas from a receptacle including a sample-receiving container arranged within a compressed-gas vessel, the sample-receiving container being double-walled, the interspace in the double wall communicating with the receptacle for cooling the sample-receiving container by the liquefied gas. The sample-receiving container is connected at its upper end to the interspace by a first valve and at its lower end to the compressed-gas vessel by a second valve. Preferably the second valve is a pressure-sensitive check valve and the two valves may be controllably interconnected.

14 Claims, 1 Drawing Figure

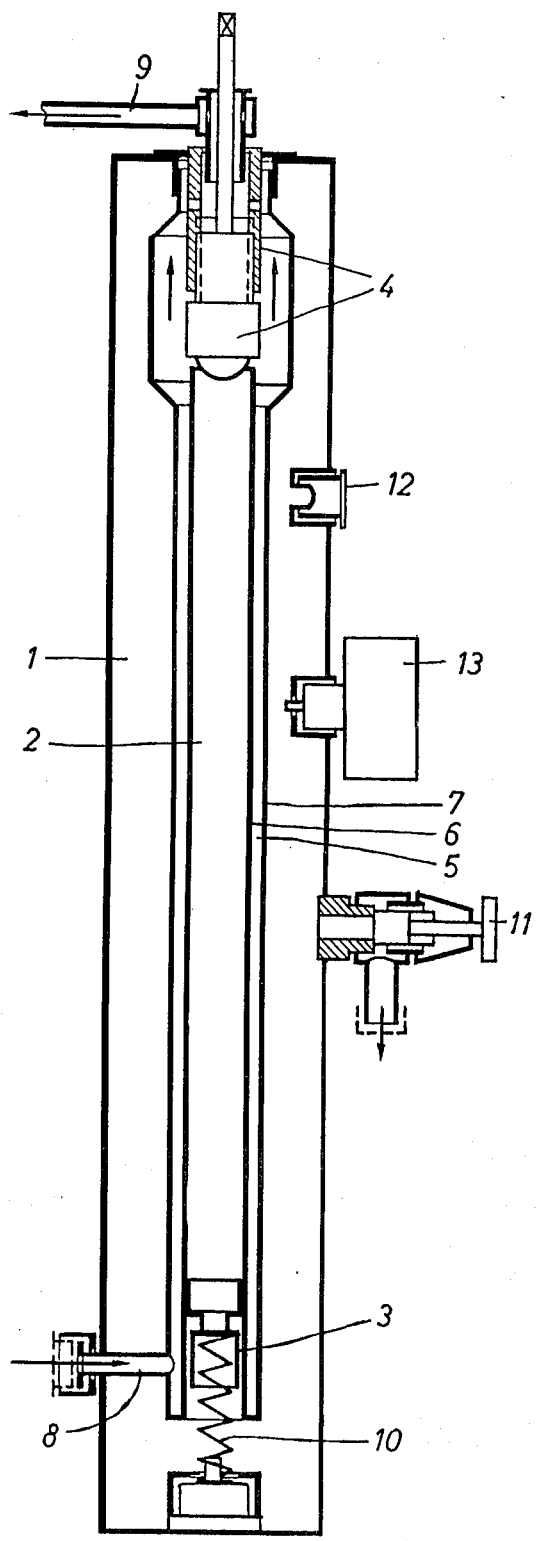

SAMPLING DEVICE FOR LIQUEFIED GASES

This invention relates to a device for withdrawing a sample of a liquefied gas from a container and for the total evaporation of the thus-withdrawn liquid for analytical purposes.

In the utilization of liquefied gases, such as, for example, liquid oxygen, liquid nitrogen, or also a liquefied noble gas, it is important to know exactly the composition of the gases, especially the proportion of dissolved impurities, e.g., hydrocarbons.

An apparatus for the sampling of liquefied gases stored in storage tanks for the purpose of an analytical determination of their composition has been known consisting of a capillary tube section disposed within the container, one end of this tube extending through the container wall and terminating in an evaporator pipe directly adjoining the container wall and provided with a heating unit. A sample analyzer, e.g., a gas chromatograph, is connected to the other end of the evaporator pipe by way of a control valve (German Patent 1,138,257).

The disadvantage of this conventional apparatus resides in that a fixed installation within the storage tank is required for its operation. As a consequence, the apparatus can only be used in conjunction with a single storage tank.

Additionally, the analysis can only be conducted at the site where the sample is withdrawn, resulting in considerable expenditure. A further disadvantage of the conventional device resides in that it is impossible to ensure with certainty that the gaseous mixture flowing toward the analyzer has the same composition as the liquid to be examined. Due to the differing boiling points of the components of the liquid evaporating in the evaporator pipe, the lower-boiling components are first primarily evaporated and flow toward the analyzer, whereas the higher-boiling components follow subsequently in concentrated form.

This invention is based on the problem of developing a simple device which can be used as a mobile unit for the sampling of a liquefied gas and for the total evaporation of the thus-withdrawn liquid wherein assurance is obtained that, after the phase conversion, the thus-produced gas has the same composition as the liquid.

This problem is solved by providing an apparatus consisting of a cooled sample-receiving container and a compressed-gas container, wherein the sample-receiving container is in communication with the tank via a first shut-off element and with the compressed-gas container by way of a second shut-off element.

According to the invention, the liquid to be tested, e.g., liquefied oxygen, liquefied nitrogen, or also a liquefied noble gas, is withdrawn from a storage tank or also directly from a corresponding low-temperature separation plant, and fed to the sample-receiving container (sampling vessel) by way of the opened first shut-off element. Since this container, just as the connection lines, is cooled at least to the boiling temperature of the liquid to be treated and, according to a further feature, is provided with a thermal insulation, no evaporation of the liquid takes place within the sample-receiving container, so that the liquid remains in its original composition.

As soon as the sample-receiving container is filled with liquid, or as soon as the liquid level in the sample-receiving container has reached a certain height, the first shut-off element is closed again, whereby the sample has now been isolated. At this point, the second shut-off element is opened, establishing a connection between the sample-receiving container and the compressed-air vessel. The liquid present in the sample-receiving container flows in its original composition from the latter container into the warm compressed-gas vessel, wherein a very rapid and complete evaporation of the transferred liquid takes place; at the same time, a certain excess pressure arises which makes it possible to feed the gas to an analyzer without any special conveying means. The thus-filled device can be transported to any desired locations in any possible manner, for example to a laboratory equipped for conducting the analysis.

It has thus been made possible by the present invention to feed a liquid to be tested, consisting of several components, without a change in its composition in the form of a gaseous mixture to an appropriate analyzing apparatus (instrument).

The second shut-off element can be operated manually or also automatically. It is also possible to couple this element with the first shut-off element. In this case, if the first shut-off element is activated, the second element will be automatically opened as soon as the first has been closed.

However, especially from a constructional viewpoint, it proved to be very advantageous to control the second shut-off element by way of the pressure in the sample-receiving container. The second shut-off element, which in this case is advantageously a check valve set to a predetermined pressure, is automatically opened as soon as the pressure in the sample-receiving container exceeds the set pressure of the check valve, so that now liquid flows into the warm compressed-gas vessel and is very quickly evaporated therein. The pressure in the sample-receiving container rises already after the vaporation of a minute portion of the collected liquid above the set pressure of the check valve, which occurs within a short period of time due to the provided introduction of heat.

Advantageously, the second shut-off element is in communication with the lower zone of the sample-receiving container, and the first shut-off element is in communication with the upper zone of this container.

Especially if the closing of the first shut-off element and the opening of the second shut-off element take place only once, the sample-receiving container is filled entirely with liquid, it is possible in a particularly simple manner to make available an exactly defined amount of liquid for purposes of analysis, the volume of this liquid corresponding exactly to the volume of the sample-receiving container.

The sample-receiving container can be cooled in any desired manner. However, it proved to be advantageous to utilize a portion of the liquid to be examined for cooling purposes. In this case, the sample-receiving container can be provided with an external jacket and an internal jacket, the interspace between both jackets being in communication, on the one hand, with the liquid tank and, on the other hand, via the first shut-off element with the sample-receiving container. Furthermore, the interspace is provided with an additional discharge line for gas or liquid. The cooling effect is now obtained by the introduction of cold liquid into the interspace. During the cooling period, wherein at least a part of the liquid in the interspace is evaporated and is discharged by way of the corresponding gas or liquid discharge line, the first shut-off element is closed. The latter is opened only after the cooling step is terminated, as registered by the exit of liquid via the gas or liquid discharge line. At this point in time, a portion of the liquid flowing in the interspace can flow, without a phase change, into the sample-receiving container.

Any suitable material can be used to provide for the thermal insulation of the sample-receiving container. However, it proved to be advantageous to employ as thermal insulation directly the atmosphere of the compressed-gas vessel, which is of poor thermal conductivity. This is achieved by arranging the sample-receiving container within the compressed-gas vessel. The apparatus of this invention is thus advantageously suitable for the accurate analysis of samples of liquified, deep-cooled gases consisting of one or more primary components and any desired number of secondary components. Moreover, the apparatus can be utilized at any location and can be transported over arbitrary distances. Accordingly, there is the possibility of examining the sample withdrawn from a tank, for example, in a laboratory located at a distance from such tank, rather than directly at the tank site.

Additional explanations of the invention can be derived from the embodiment schematically illustrated in the FIGURE.

According to the drawing, a sample-receiving container is disposed within a compressed-gas vessel 1. The lower zone of the sample-receiving container 2 is connected, by way of a check valve 3, with the inner space of the compressed-gas vessel 1, while the upper zone is in communication, via a valve 4, with the interspace 5 formed by the walls 6 and 7 of the sample-receiving container 2. The interspace 5 is additionally equipped with a connection 8 in communication, during the sample withdrawal, with a tank containing the liquid to be tested. Moreover, the interspace 5 is in communication with a gas or liquid discharge conduit 9. During the sampling step, the connection 8 is coupled to a tank containing the liquid to be examined, so that the liquid now flows under minor excess pressure into the interspace 5 by way of the connection 8. In the interspace 5, the liquid is at least partially evaporated in heat exchange with the sample-receiving container 2 which is initially still warm. The thus-produced liquid-vapor mixture is withdrawn from the interspace by way of conduit 9. As soon as the sample-receiving container is cooled to at least the boiling point of the liquid, which is the case when a uniform stream of liquid exits from conduit 9, the valve 4 is opened so that now a portion of the liquid flows into the sample-receiving container 2 and fills same within a specific period of time up to the top rim which simultaneously forms the valve seat. Once the sample-receiving container 2 is completely filled with the liquid, the valve 4 is closed. As a consequence, the pressure in the sample-receiving container will now rise already by the evaporation of a very small amount of liquid.

As soon as the pressure in the sample-receiving container effective upon the check valve 3 exceeds the set pressure of the check valve 3, predetermined by the bias of the spring 10, the check valve opens and the collected liquid flows into the compressed gas vessel 1 wherein a very rapid and complete evaporation takes place. In the compressed-gas vessel, a gas is now present which corresponds exactly to the composition of the liquid. This gas can then be withdrawn via the valve 11 and subjected to immediate analysis. However, it is also possible to transport the entire apparatus into a laboratory and conduct the analysis of the gas only at that location.

For safety reasons and for monitoring purposes, the compressed-gas vessel is additionally provided with a bursting disc 12 and a manometer 13.

Due to the fact that the valve 4 is closed only once the sample-receiving container is filled completely with liquid it is made possible to provide an exactly predetermined quantity of liquid for analysis purposes, the volume of this liquid corresponding exactly to the volume of the sample-receiving container.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A device for sampling a liquified gas from a receptacle and for the total evaporation of the thus-withdrawn liquid comprising:
   a cooled sample-receiving container;
   a compressed-gas vessel;
   first controllable communication means, including a first valve, between said sample-receiving container and said receptacle; and
   second controllable communication means, including a second valve, between said sample-receiving container and said compressed-gas vessel for releasing said liquified gas in the liquid phase into said compressed-gas vessel for evaporation therein.

2. The device according to claim 2, wherein said sample-receiving container is thermally insulated.

3. The device according to claim 2, wherein said sample-receiving container is arranged within said compressed-gas vessel and wherein the atmosphere of said compressed gas vessel provides the thermal insulation for said sample-receiving container.

4. The device according to claim 3, wherein said sample-receiving container includes an external jacket and an internal jacket forming a double-wall with an interspace therebetween and wherein said interspace forms a portion of said first communication means between said receptacle and said first valve.

5. The device according to claim 4, wherein said sample-receiving container includes an upper zone and a lower zone and wherein said first valve establishes connection to said upper zone and said second valve establishes connection to said lower zone.

6. The device according to claim 1, wherein said second valve is a pressure-sensitive check valve.

7. The device according to claim 4, wherein said second valve is a pressure-sensitive check valve.

8. The device according to claim 5, wherein said second valve is a pressure-sensitive check valve.

9. The device according to claim 1, also including means for controllably connecting said first valve with said second valve.

10. The device according to claim 4, also including a discharge conduit for said interspace.

11. A method for transferring a sample of a liquid from a receptacle to a compressed-gas vessel comprising the steps:
    providing a double-walled sample-receiving container with the compressed-gas vessel;
    insulating the sample-receiving container with the atmosphere of the compressed-gas vessel;

venting said liquid between the double walls of the sample-receiving container until the sample-receiving container is cooled at least to the boiling point of the said liquid;

filling the cooled sample-receiving container with the said liquid;

releasing at least a portion of said liquid from the sample-receiving container into the compressed gas vessel; and evaporating said released liquid in the compressed-gas vessel.

12. A method according to claim 11, wherein the step of filling the cooled sample-receiving container includes the step of automatically measuring a precise amount of the said liquid.

13. A method according to claim 12, also including after the step of filling, the step of automatically releasing the contents of the sample-receiving container at a predetermined pressure.

14. A method according to claim 11, wherein said liquid is a cryogenic liquid having a normal boiling point below 0° C.

* * * * *